US012227772B2

(12) United States Patent
Farrell et al.

(10) Patent No.: US 12,227,772 B2
(45) Date of Patent: Feb. 18, 2025

(54) MODIFIED STEROL ACYLTRANSFERASES

(71) Applicant: DSM IP ASSETS B.V., Heerlen (NL)

(72) Inventors: Christopher Mark Farrell, Columbia, MD (US); Lisa Ann Laprade, Columbia, MD (US); Otto Martin Lehmann, Kaiseraugst (CH); Joshua Trueheart, Columbia, MD (US)

(73) Assignee: DSM IP ASSETS B.V., Heerlen (NL)

( * ) Notice: Subject to any disclaimer, the term of this patent is extended or adjusted under 35 U.S.C. 154(b) by 891 days.

(21) Appl. No.: 17/050,603

(22) PCT Filed: May 21, 2019

(86) PCT No.: PCT/EP2019/063076
§ 371 (c)(1),
(2) Date: Oct. 26, 2020

(87) PCT Pub. No.: WO2019/224187
PCT Pub. Date: Nov. 28, 2019

(65) Prior Publication Data
US 2021/0115412 A1 Apr. 22, 2021

(30) Foreign Application Priority Data
May 22, 2018 (CH) .......................... 627/18

(51) Int. Cl.
*C12N 9/10* (2006.01)
*C12P 33/00* (2006.01)

(52) U.S. Cl.
CPC ............ *C12N 9/1029* (2013.01); *C12P 33/00* (2013.01); *C12Y 203/01026* (2013.01)

(58) Field of Classification Search
CPC .... C12N 9/1029; C12N 15/52; C12N 9/1025; C12P 33/00; C12Y 203/01026; C12Y 103/01072
See application file for complete search history.

(56) References Cited

U.S. PATENT DOCUMENTS 7,608,421 B2  10/2009 Lang et al.

FOREIGN PATENT DOCUMENTS

| CA | 2773030 A1 | 3/2011 |
|---|---|---|
| CN | 101052706 A | 10/2007 |
| CN | 102812124 A | 12/2012 |
| CN | 107189954 A | 9/2017 |
| JP | 2003-508052 | 3/2003 |
| JP | 2007-516717 | 6/2007 |
| JP | 2010-534479 | 11/2010 |
| JP | 2012-24084 | 2/2012 |
| JP | 2013-502903 | 1/2013 |
| WO | WO 01/16308 | 3/2001 |
| WO | 03/064650 | 8/2003 |
| WO | WO 2005/066347 | 7/2005 |
| WO | 2006009434 A1 | 1/2006 |
| WO | WO 2009/015314 | 1/2009 |
| WO | WO 2011/023298 | 3/2011 |
| WO | 2011/067144 | 6/2011 |
| WO | 2013081456 A2 | 6/2013 |
| WO | 2017/108799 | 6/2017 |
| WO | WO 2017108799 A1 * | 6/2017 |

OTHER PUBLICATIONS

Chen et al. Genomics-driven discovery of the pneumocandin biosynthetic gene cluster in the fungus *Glarea lozoyensis*. BMC Genomics (2013): 14:339). (Year: 2013).*
Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
International Search Report for PCT/EP2019/063076 dated Aug. 2, 2019, 5 pages.
Written Opinion of the ISA for PCT/EP2019/063076 dated Aug. 2, 2019, 6 pages.
Yu et al., "Molecular Cloning and Characterization of Two Isoforms of *Saccharomyces cerevisiae* Acyl-CoA:Sterol Acyltransferase", The Journal of Biological Chemistry, Sep. 27, 1996, vol. 271, No. 39, XP002094336, pp. 24157-24163 (7 total pages).
Zweytick et al., "Contribution of Are1p and Are2p to steryl ester synthesis in the yeast *Saccharomyces cerevisiae*", European Journal of Biochemistry, Feb. 1, 2000, vol. 267, No. 4, XP055059359, pp. 1075-1082, (8 total pages).
Wriessnegger et al., "Yeast metabolic engineering—Targeting sterol metabolism and terpenoid formation", Progress in Lipid Research, Apr. 6, 2013, vol. 52, No. 3, XP028553555, pp. 277-293 (17 total pages).
Sambroook, "Molecular Cloning, A Laboratory Manual", Second Edition, 1989, table of contents (30 total pages).
Ausubel et al., "Current Protocols in Molecular Biology", Nov. 1988, table of contents (3 total pages).
Rice et al., "EMBOSS: The European Molecular Biology Open Software Suite", The European Molecular Biology Open Software Suite, Trends in Genetics, Jun. 2000, vol. 16, No. 6, pp. 276-277 (2 total pages).

* cited by examiner

*Primary Examiner* — Iqbal H Chowdhury
(74) *Attorney, Agent, or Firm* — Nixon & Vanderhye, PC

(57) ABSTRACT

The present invention is related to modified sterol acyltransferase enzymes with improved activity and/or specificity towards acylation of the vitamin D3 precursor 7-dehydrocholesterol (7-DHC) to be used in biotechnological production of vitamin D3. The invention further relates to a yeast strain expressing said modified enzymes and their use in a process for production of vitamin D3 or derivatives and/or metabolites thereof.

10 Claims, No Drawings
Specification includes a Sequence Listing.

```
                        SEQUENCE LISTING

<160> NUMBER OF SEQ ID NOS: 15

<210> SEQ ID NO 1
<211> LENGTH: 610
<212> TYPE: PRT
<213> ORGANISM: Saccharomyces cerevisiae

<400> SEQUENCE: 1

Met Thr Glu Thr Lys Asp Leu Leu Gln Asp Glu Glu Phe Leu Lys Ile
1               5                   10                  15

Arg Arg Leu Asn Ser Ala Glu Ala Asn Lys Arg His Ser Val Thr Tyr
            20                  25                  30

Asp Asn Val Ile Leu Pro Gln Glu Ser Met Glu Val Ser Pro Arg Ser
        35                  40                  45

Ser Thr Thr Ser Leu Val Glu Pro Val Glu Ser Thr Glu Gly Val Glu
    50                  55                  60

Ser Thr Glu Ala Glu Arg Val Ala Gly Lys Gln Glu Gln Glu Glu Glu
65                  70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
            100                 105                 110

Phe Phe Gly Asp Val Ser Phe Asp Pro Arg Pro Thr Leu Leu Asp Ser
        115                 120                 125

Ala Ile Asn Val Pro Phe Gln Thr Thr Phe Lys Gly Pro Val Leu Glu
    130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175

Pro Pro Gly Glu Lys Leu Glu Ser Asn Phe Ser Gly Ile Tyr Val Phe
            180                 185                 190

Ala Trp Met Phe Leu Gly Trp Ile Ala Ile Arg Cys Cys Thr Asp Tyr
        195                 200                 205
```

-continued

```
Tyr Ala Ser Tyr Gly Ser Ala Trp Asn Lys Leu Glu Ile Val Gln Tyr
    210                 215                 220
Met Thr Thr Asp Leu Phe Thr Ile Ala Met Leu Asp Leu Ala Met Phe
225                 230                 235                 240
Leu Cys Thr Phe Phe Val Val Phe Val His Trp Leu Val Lys Lys Arg
                245                 250                 255
Ile Ile Asn Trp Lys Trp Thr Gly Phe Val Ala Val Ser Ile Phe Glu
            260                 265                 270
Leu Ala Phe Ile Pro Val Thr Phe Pro Ile Tyr Val Tyr Tyr Phe Asp
        275                 280                 285
Phe Asn Trp Val Thr Arg Ile Phe Leu Phe Leu His Ser Val Val Phe
    290                 295                 300
Val Met Lys Ser His Ser Phe Ala Phe Tyr Asn Gly Tyr Leu Trp Asp
305                 310                 315                 320
Ile Lys Gln Glu Leu Glu Tyr Ser Ser Lys Gln Leu Gln Lys Tyr Lys
                325                 330                 335
Glu Ser Leu Ser Pro Glu Thr Arg Glu Ile Leu Gln Lys Ser Cys Asp
            340                 345                 350
Phe Cys Leu Phe Glu Leu Asn Tyr Gln Thr Lys Asp Asn Asp Phe Pro
        355                 360                 365
Asn Asn Ile Ser Cys Ser Asn Phe Phe Met Phe Cys Leu Phe Pro Val
    370                 375                 380
Leu Val Tyr Gln Ile Asn Tyr Pro Arg Thr Ser Arg Ile Arg Trp Arg
385                 390                 395                 400
Tyr Val Leu Glu Lys Val Cys Ala Ile Ile Gly Thr Ile Phe Leu Met
                405                 410                 415
Met Val Thr Ala Gln Phe Phe Met His Pro Val Ala Met Arg Cys Ile
            420                 425                 430
Gln Phe His Asn Thr Pro Thr Phe Gly Gly Trp Ile Pro Ala Thr Gln
        435                 440                 445
Glu Trp Phe His Leu Leu Phe Asp Met Ile Pro Gly Phe Thr Val Leu
    450                 455                 460
Tyr Met Leu Thr Phe Tyr Met Ile Trp Asp Ala Leu Leu Asn Cys Val
465                 470                 475                 480
Ala Glu Leu Thr Arg Phe Ala Asp Arg Tyr Phe Tyr Gly Asp Trp Trp
                485                 490                 495
Asn Cys Val Ser Phe Glu Glu Phe Ser Arg Ile Trp Asn Val Pro Val
            500                 505                 510
His Lys Phe Leu Leu Arg His Val Tyr His Ser Ser Met Gly Ala Leu
        515                 520                 525
His Leu Ser Lys Ser Gln Ala Thr Leu Phe Thr Phe Phe Leu Ser Ala
    530                 535                 540
Val Phe His Glu Met Ala Met Phe Ala Ile Phe Arg Arg Val Arg Gly
545                 550                 555                 560
Tyr Leu Phe Met Phe Gln Leu Ser Gln Phe Val Trp Thr Ala Leu Ser
                565                 570                 575
Asn Thr Lys Phe Leu Arg Ala Arg Pro Gln Leu Ser Asn Val Val Phe
            580                 585                 590
Ser Phe Gly Val Cys Ser Gly Pro Ser Ile Ile Met Thr Leu Tyr Leu
        595                 600                 605
Thr Leu
610
```

<210> SEQ ID NO 2
<211> LENGTH: 1833
<212> TYPE: DNA
<213> ORGANISM: Saccharomyces cerevisiae

<400> SEQUENCE: 2

| | | | | | | |
|---|---|---|---|---|---|---|
| atgacggaga | ctaaggattt | gttgcaagac | gaagagtttc | ttaagatccg | cagactcaat | 60 |
| tccgcagaag | ccaacaaacg | gcattcggtc | acgtacgata | acgtgatcct | gccacaggag | 120 |
| tccatggagg | tttcgccacg | gtcgtctacc | acgtcgctgg | tggagccagt | ggagtcgact | 180 |
| gaaggagtgg | agtcgactga | ggcggaacgt | gtggcaggga | agcaggagca | ggaggaggag | 240 |
| taccctgtgg | acgcccacat | gcaaaagtac | cttccacacc | tgaagagcaa | gtctcggtcg | 300 |
| aggttccacc | gaaaggatgc | tagcaagtat | gtgtcgtttt | tggggacgt | gagttttgat | 360 |
| cctcgcccca | cgctcctgga | cagcgccatc | aacgtgccct | tccagacgac | tttcaaaggt | 420 |
| ccggtgctgg | agaaacagct | caaaaattta | cagttgacaa | agaccaagac | caaggccacg | 480 |
| gtgaagacta | cggtgaagac | tacggagaaa | acggacaagg | cagatgcccc | ccaggagaa | 540 |
| aaactggagt | cgaacttttc | agggatctac | gtgttcgcat | ggatgttctt | gggctggata | 600 |
| gccatcaggt | gctgcacaga | ttactatgcg | tcgtacggca | gtgcatggaa | taagctggaa | 660 |
| atcgtgcagt | acatgacaac | ggacttgttc | acgatcgcaa | tgttggactt | ggcaatgttc | 720 |
| ctgtgcactt | tcttcgtggt | tttcgtgcac | tggctggtga | aaaagcggat | catcaactgg | 780 |
| aagtggactg | ggttcgttgc | agtgagcatc | ttcgagttgg | ctttcatccc | cgtgacgttc | 840 |
| cccatttacg | tctactactt | tgatttcaac | tgggtcacga | aatcttcct | gttcctgcac | 900 |
| tccgtggtgt | tgttatgaa | gagccactcg | tttgcctttt | acaacgggta | tctttgggac | 960 |
| ataaagcagg | aactcgagta | ctcttccaaa | cagttgcaaa | aatacaagga | atctttgtcc | 1020 |
| ccagagaccc | gcgagattct | gcaaaaaagt | tgcgactttt | gccttttcga | attgaactac | 1080 |
| cagaccaagg | ataacgactt | ccccaacaac | atcagttgca | gcaatttctt | catgttctgt | 1140 |
| tgttccccg | tcctcgtgta | ccagatcaac | tacccaagaa | cgtcgcgcat | cagatggagg | 1200 |
| tatgtgttgg | agaaggtgtg | cgccatcatt | ggcaccatct | tcctcatgat | ggtcacggca | 1260 |
| cagttcttca | tgcacccggt | ggccatgcgc | tgtatccagt | tccacaacac | gcccaccttc | 1320 |
| ggcggctgga | tccccgccac | gcaagagtgg | ttccacctgc | tcttcgacat | gattccgggc | 1380 |
| ttcactgttc | tgtacatgct | cacgtttac | atgatatggg | acgctttatt | gaattgcgtg | 1440 |
| gcggagttga | ccaggtttgc | ggacagatat | ttctacggcg | actggtggaa | ttgcgtttcg | 1500 |
| tttgaagagt | ttagcagaat | ctggaacgtc | cccgttcaca | aatttttact | aagacacgtg | 1560 |
| taccacagct | ccatgggcgc | attgcatttg | agcaagagcc | aagctacatt | atttactttt | 1620 |
| ttcttgagtg | ccgtgttcca | cgaaatggcc | atgttcgcca | ttttcagaag | ggttagagga | 1680 |
| tatctgttca | tgttccaact | gtcgcagttt | gtgtggactg | ctttgagcaa | caccaagttt | 1740 |
| ctacgggcaa | gaccgcagtt | gtccaacgtt | gtcttttcgt | tggtgtctg | ttcagggccc | 1800 |
| agtatcatta | tgacgttgta | cctgaccta | tga | | | 1833 |

<210> SEQ ID NO 3
<211> LENGTH: 642
<212> TYPE: PRT
<213> ORGANISM: Saccharomyces cerevisiae

<400> SEQUENCE: 3

```
Met Asp Lys Lys Lys Asp Leu Leu Glu Asn Glu Gln Phe Leu Arg Ile
1               5                   10                  15

Gln Lys Leu Asn Ala Ala Asp Ala Gly Lys Arg Gln Ser Ile Thr Val
            20                  25                  30

Asp Asp Glu Gly Glu Leu Tyr Gly Leu Asp Thr Ser Gly Asn Ser Pro
        35                  40                  45

Ala Asn Glu His Thr Ala Thr Thr Ile Thr Gln Asn His Ser Val Val
    50                  55                  60

Ala Ser Asn Gly Asp Val Ala Phe Ile Pro Gly Thr Ala Thr Glu Gly
65                  70                  75                  80

Asn Thr Glu Ile Val Thr Glu Val Ile Glu Thr Asp Asp Asn Met
                85                  90                  95

Phe Lys Thr His Val Lys Thr Leu Ser Ser Lys Glu Lys Ala Arg Tyr
                100                 105                 110

Arg Gln Gly Ser Ser Asn Phe Ile Ser Tyr Phe Asp Asp Met Ser Phe
            115                 120                 125

Glu His Arg Pro Ser Ile Leu Asp Gly Ser Val Asn Glu Pro Phe Lys
        130                 135                 140

Thr Lys Phe Val Gly Pro Thr Leu Glu Lys Glu Ile Arg Arg Arg Glu
145                 150                 155                 160

Lys Glu Leu Met Ala Met Arg Lys Asn Leu His His Arg Lys Ser Ser
                165                 170                 175

Pro Asp Ala Val Asp Ser Val Gly Lys Asn Asp Gly Ala Ala Pro Thr
            180                 185                 190

Thr Val Pro Thr Ala Ala Thr Ser Glu Thr Val Val Thr Val Glu Thr
        195                 200                 205

Thr Ile Ile Ser Ser Asn Phe Ser Gly Leu Tyr Val Ala Phe Trp Met
    210                 215                 220

Ala Ile Ala Phe Gly Ala Val Lys Ala Leu Ile Asp Tyr Tyr Tyr Gln
225                 230                 235                 240

His Asn Gly Ser Phe Lys Asp Ser Glu Ile Leu Lys Phe Met Thr Thr
                245                 250                 255

Asn Leu Phe Thr Val Ala Ser Val Asp Leu Leu Met Tyr Leu Ser Thr
            260                 265                 270

Tyr Phe Val Val Gly Ile Gln Tyr Leu Cys Lys Trp Gly Val Leu Lys
        275                 280                 285

Trp Gly Thr Thr Gly Trp Ile Phe Thr Ser Ile Tyr Glu Phe Leu Phe
    290                 295                 300

Val Ile Phe Tyr Met Tyr Leu Thr Glu Asn Ile Leu Lys Leu His Trp
305                 310                 315                 320

Leu Ser Lys Ile Phe Leu Phe Leu His Ser Leu Val Leu Leu Met Lys
                325                 330                 335

Met His Ser Phe Ala Phe Tyr Asn Gly Tyr Leu Trp Gly Ile Lys Glu
            340                 345                 350

Glu Leu Gln Phe Ser Lys Ser Ala Leu Ala Lys Tyr Lys Asp Ser Ile
        355                 360                 365

Asn Asp Pro Lys Val Ile Gly Ala Leu Glu Lys Ser Cys Glu Phe Cys
    370                 375                 380

Ser Phe Glu Leu Ser Ser Gln Ser Leu Ser Asp Gln Thr Gln Lys Phe
385                 390                 395                 400
```

```
Pro Asn Asn Ile Ser Ala Lys Ser Phe Phe Trp Thr Met Phe Pro
                405                 410                 415

Thr Leu Ile Tyr Gln Ile Glu Tyr Pro Arg Thr Lys Glu Ile Arg Trp
            420                 425                 430

Ser Tyr Val Leu Glu Lys Ile Cys Ala Ile Phe Gly Thr Ile Phe Leu
            435                 440                 445

Met Met Ile Asp Ala Gln Ile Leu Met Tyr Pro Val Ala Met Arg Ala
        450                 455                 460

Leu Ala Val Arg Asn Ser Glu Trp Thr Gly Ile Leu Asp Arg Leu Leu
465                 470                 475                 480

Lys Trp Val Gly Leu Leu Val Asp Ile Val Pro Gly Phe Ile Val Met
                485                 490                 495

Tyr Ile Leu Asp Phe Tyr Leu Ile Trp Asp Ala Ile Leu Asn Cys Val
            500                 505                 510

Ala Glu Leu Thr Arg Phe Gly Asp Arg Tyr Phe Tyr Gly Asp Trp Trp
        515                 520                 525

Asn Cys Val Ser Trp Ala Asp Phe Ser Arg Ile Trp Asn Ile Pro Val
530                 535                 540

His Lys Phe Leu Leu Arg His Val Tyr His Ser Ser Met Ser Ser Phe
545                 550                 555                 560

Lys Leu Asn Lys Ser Gln Ala Thr Leu Met Thr Phe Phe Leu Ser Ser
                565                 570                 575

Val Val His Glu Leu Ala Met Tyr Val Ile Phe Lys Lys Leu Arg Phe
            580                 585                 590

Tyr Leu Phe Phe Gln Met Leu Gln Met Pro Leu Val Ala Leu Thr
        595                 600                 605

Asn Thr Lys Phe Met Arg Asn Arg Thr Ile Ile Gly Asn Val Ile Phe
        610                 615                 620

Trp Leu Gly Ile Cys Met Gly Pro Ser Val Met Cys Thr Leu Tyr Leu
625                 630                 635                 640

Thr Phe

<210> SEQ ID NO 4
<211> LENGTH: 1929
<212> TYPE: DNA
<213> ORGANISM: Saccharomyces cerevisiae

<400> SEQUENCE: 4
atggacaaga agaaggatct actggagaac gaacaatttc tccgcatcca aaagctcaac     60
gctgccgatg cgggcaaaag acaatctata acagtggacg acgagggcga actatatggg    120
ttagacacct ccggcaactc accagccaat gaacacacag ctaccacaat tacacagaat    180
cacagcgtgg tggcctcaaa cggagacgtc gcattcatcc aggaactgc taccgaaggc     240 aatacagaga ttgtaactga agaagtgatt gagaccgatg ataacatgtt caagacccat    300
gtgaagactt taagctccaa agagaaggca cggtataggc aagggtcctc taactttata    360
tcgtatttcg atgatatgtc atttgaacac aggcccagta tattagatgg gtcagttaac    420
gagcccttca agaccaaatt cgtgggacct actttagaaa aggagatcag aagaagggag    480
aaagagctaa tggccatgcg caaaaattta caccaccgca gtcctcccc agatgctgtc     540 gactcagtag ggaaaaatga tggcgccgcc ccaactactg ttccaactgc cgccacctca    600
gaaacggtgg tcaccgttga aaccaccata atttcatcca atttctccgg ttgtacgtg     660 gcgttttgga tggctattgc atttggtgct gtcaaggctt aatagacta ttattaccag     720
```

-continued

```
cataatggta gcttcaagga ttcggagatc ttgaaattta tgactacgaa tttgttcact      780
gtggcatccg tagatctttt gatgtatttg agcacttatt ttgtcgttgg aatacaatac      840
ttatgcaagt gggggtctt gaaatggggc actaccggct ggatcttcac ctcaatttac       900
gagttttgt ttgttatctt ctacatgtat ttaacagaaa acatcctaaa actacactgg       960
ctgtccaaga tcttccttt tttgcattct ttagtttat tgatgaaaat gcattctttc       1020
gccttctaca atggctatct atggggtata aaggaagaac tacaattttc caaagcgct      1080
cttgccaaat acaaggattc tataaatgat ccaaaagtta ttggtgctct tgagaaaagc     1140
tgtgagtttt gtagttttga attgagctct cagtctttaa gcgaccaaac tcaaaaattc     1200
cccaacaata tcagtgcaaa aagctttttt tggttcacca tgtttccaac cctaatttac     1260
caaattgaat atccaagaac taaggaaatc agatggagct acgtattaga aaagatctgc     1320
gccatcttcg gtaccatttt cttaatgatg atagatgctc aaatcttgat gtatcctgta     1380
gcaatgagag cattggctgt gcgcaattct gaatggactg gtatattgga tagattattg     1440
aaatggggttg gattgctcgt tgatatcgtc ccagggttta tcgtgatgta catcttggac    1500
ttctatttga tttgggatgc cattttgaac tgtgtggctg aattgacaag atttggcgac    1560
agatatttct acggtgactg gtggaattgt gttagttggg cagacttcag tagaatttgg    1620
aacatcccag tgcataagtt tttgttaaga catgtttacc atagttcaat gagttcattc    1680
aaattgaaca agagtcaagc aactttgatg accttttct taagttccgt cgttcatgaa     1740
ttagcaatgt acgttatctt caagaaattg aggttttact tgttcttctt ccaaatgctg    1800
caaatgccat tagtagcttt aacaaatact aaattcatga ggaacagaac cataatcgga    1860
aatgttatt tctggctcgg tatctgcatg ggaccaagtg tcatgtgtac gttgtacttg     1920
acattctaa                                                            1929
```

<210> SEQ ID NO 5
<211> LENGTH: 241
<212> TYPE: PRT
<213> ORGANISM: Ustilago maydis

<400> SEQUENCE: 5

```
Met Ala Ser His Arg Pro Arg Ser Asn Lys Ala Ala Asn Gly Ala Ser
1               5                   10                  15

Thr Ser Pro Lys Arg Ser Trp Ile Ile Val Ser Ala Ala Leu Val Gly
            20                  25                  30

Phe Cys Ala Leu Ile Ala Ala Leu Asp Ser Ile Arg Ser Ser Phe Tyr
        35                  40                  45

Ile Phe Asp His Lys Ala Ile Tyr Lys Ile Ala Ser Thr Ala Val Ala
    50                  55                  60

Asn His Pro Gly Asn Ala Thr Ala Ile Phe Asp Asp Val Leu Asp Asn
65                  70                  75                  80

Leu Arg Ala Asp Pro Lys Leu Ala Pro Tyr Ile Asn Lys Asn His Phe
                85                  90                  95

Ser Asp Glu Ser Glu Trp Met Phe Asn Asn Ala Gly Gly Ala Met Gly
            100                 105                 110

Ser Met Phe Ile Ile His Ala Ser Val Thr Glu Tyr Leu Ile Phe Phe
        115                 120                 125

Gly Thr Pro Val Gly Thr Glu Gly His Thr Gly Arg His Thr Ala Asp
    130                 135                 140
```

Asp Tyr Phe Asn Ile Leu Thr Gly Asn Gln Tyr Ala Phe Pro Ala Gly
145                 150                 155                 160

Ala Leu Lys Ala Glu His Tyr Pro Ala Gly Ser Val His His Leu Arg
            165                 170                 175

Arg Gly Thr Val Lys Gln Tyr Met Met Pro Glu Asp Gly Cys Trp Ala
        180                 185                 190

Leu Glu Leu Ala Gln Gly Trp Ile Pro Pro Met Leu Pro Phe Gly Leu
    195                 200                 205

Ala Asp Val Leu Ser Ser Thr Leu Asp Leu Pro Thr Phe Gly Ile Thr
210                 215                 220

Val Trp Ile Thr Ala Arg Glu Met Val Gly Asn Leu Leu Ile Gly Lys
225                 230                 235                 240

Phe

<210> SEQ ID NO 6
<211> LENGTH: 726
<212> TYPE: DNA
<213> ORGANISM: Ustilago maydis

<400> SEQUENCE: 6
atggcatcgc atagaccacg cagcaacaag gctgccaatg gtgcttcgac ttcacccaaa       60
cgcagctgga taattgtctc agctgcgctc gttggcttct gcgctctcat cgccgctctc     120
gattcgatcc gatccagctt ctacatcttt gaccacaagg caatctacaa gatcgcatcg     180
actgcggtcg ccaaccatcc aggcaatgcg acggccatct ttgatgatgt cctcgacaac     240
cttcgtgccg accccaagct cgcgccttac atcaacaaga tcatttcag cgacgagtca      300 gaatggatgt tcaacaatgc cggtggtgct atgggtagca tgttcatcat tcatgcttcc     360
gtcaccgagt acctgatctt ctttggcact cccgtcggaa ccgagggtca cactggtcgt     420
cacacagccg atgactactt caacatcctt accggtaacc aatacgcttt ccagctggt     480 gcgctcaagg cggagcacta ccctgccgga tcagtgcacc atcttcgccg cggaacggtc     540
aagcagtaca tgatgcctga agacggctgc tgggcgctcg agcttgctca gggctggatc     600
ccacccatgc ttccctttgg tctcgccgat gtgctcagct cgacgctcga cctgcccacc     660
tttggtatca ctgtctggat cactgcacga gaaatggttg gcaatctgct catcggcaag     720
ttttga                                                                726

<210> SEQ ID NO 7
<211> LENGTH: 384
<212> TYPE: PRT
<213> ORGANISM: Pichia pastoris

<400> SEQUENCE: 7

Met Asp Ile Ala Leu Glu Ile Leu Asp Thr Phe Val Phe Asp Lys Val
1               5                   10                  15

Tyr Ala Lys Leu Leu Pro Ile Ser Leu Val Gln His Leu Pro Asp Gly
            20                  25                  30

Tyr Leu Lys Thr Leu Gly His Leu Thr Gly Ala Asn Asn Thr Met Glu
        35                  40                  45

Ser Leu Phe Gly Ile Ala Pro Asn Val Asp Gln Ala Ser Lys Asn His
    50                  55                  60

Trp Leu Arg Thr Val Asn Asp Ser Ile Ala Leu Ala Arg Pro Gly Glu
65                  70                  75                  80

```
Arg Leu Val Tyr Gly Val Asn Ala Pro Leu His Phe Phe Asp Glu Thr
                85                  90                  95
Ala Tyr Thr Tyr Ala Ser Ile Leu Gly Arg Ser Asn Ile Ile Arg Gln
            100                 105                 110
Phe Thr Thr Leu Met Ile Leu Met Ile Leu Phe Gly Trp Gly Leu Tyr
        115                 120                 125
Leu Ser Val Ala Ser Phe Ser Tyr Tyr Phe Val Phe Asp Lys Ala Ile
    130                 135                 140
Phe Asn His Pro Arg Tyr Leu Lys Asn Gln Met Ser Leu Glu Ile His
145                 150                 155                 160
Gln Ala Leu Thr Ala Ile Pro Thr Met Val Leu Leu Thr Val Pro Trp
                165                 170                 175
Phe Leu Ile Glu Leu Arg Gly Tyr Ser Lys Leu Tyr Phe Asp Val Asn
            180                 185                 190
Glu Ser Thr Gly Gly Trp Lys Ala Ile Ile Trp Gln Ile Pro Cys Phe
        195                 200                 205
Ile Met Phe Thr Asp Cys Cys Ile Tyr Phe Ile His Arg Trp Leu His
    210                 215                 220
Trp Pro Ser Val Tyr Lys Arg Leu His Lys Pro His Lys Trp Ile
225                 230                 235                 240
Val Cys Thr Pro Phe Ala Ser His Ala Phe His Pro Val Asp Gly Tyr
                245                 250                 255
Ala Gln Ser Leu Pro Tyr His Leu Tyr Gly Met Leu Phe Pro Leu His
            260                 265                 270
Lys Val Ser Tyr Leu Ile Leu Phe Gly Leu Val Asn Phe Trp Thr Val
        275                 280                 285
Met Ile His Asp Gly Glu Tyr Leu Ser Arg Asp Pro Ile Val Asn Gly
    290                 295                 300
Ala Ala Cys His Thr Val His His Leu Tyr Phe Asn Tyr Asn Tyr Gly
305                 310                 315                 320
Gln Phe Thr Thr Leu Trp Asp Arg Leu Gly Gly Ser Tyr Arg Met Pro
                325                 330                 335
Asp Lys Glu Leu Phe Asp Lys Asn Lys Lys Asp Val Lys Thr Trp
            340                 345                 350
Arg Ser Gln Val Lys Gln Ala Asp Ser Ile Arg Glu Asp Leu Glu Gly
        355                 360                 365
Lys Glu Asp Phe Arg Glu Tyr Gly Thr Glu Glu Lys Leu Lys Ser Thr
    370                 375                 380

<210> SEQ ID NO 8
<211> LENGTH: 1155
<212> TYPE: DNA
<213> ORGANISM: Pichia pastoris

<400> SEQUENCE: 8
atggacattg ctttggagat tctagacact tttgtctttg acaaagtcta tgcaaaacta    60
ctgcccattt ctctggtgca acatttgcca gatggctatt tgaagacttt gggacatttg   120
actggtgcca acaacaccat ggaatcactg ttcggaatag ctccaaacgt tgaccaagcg   180
tctaagaacc actggctgag aacagtgaat gactctattg ccttagcccg tcccggtgag   240
cgtctggtct acggtgtcaa cgctccttta cactttttg acgaaacagc gtatacatac   300
gcatcgatct tggacgctc caatatcatt cgacaattca aactttgat gattctgatg   360 attcttttg ctgggttt gtatttatct gtggcttcat tttcatacta ctttgttttt   420
```

```
gataaagcca ttttcaatca cccaagatac ctcaaaaacc agatgtctct ggagatccat    480
caagcgttga ctgctatacc tacgatggtt ttgcttacag ttccatggtt tttgattgag    540
ttgcgtggat actctaaatt atactttgat gtaaatgagt ctactggagg atggaaggct    600
attatttggc aaaattccttg cttcattatg tttaccgatt gttgtatcta ctttattcat    660
```

```
cgttggttgc actggccatc cgtgtataag cgtttgcaca agcctcacca caagtggatt    720
gtttgtacac cttttgctag tcatgccttc catccagttg atggttatgc acaatcacta    780
ccttaccatt tgtatggaat gttgtttcca ctacacaagg tgagctatct gatcttattt    840
gggcttgtga acttttggac tgttatgatc catgatggaa atacctgtc cagagaccct     900 atagtcaatg gagctgcttg tcatacagtg catcacctat acttcaacta caattacggc    960
cagttcacaa cactttggga ccgtcttggt ggatcataca gaatgccaga caaggaactc    1020
tttgataaga acaagaagaa agatgtaaag acatggcgtt cacaagtcaa gcaggccgat    1080
tcgataagag aagacttaga gggaaaagaa gatttccgtg agtatggaac tgaggaaaaa    1140
cttaaaagca catag                                                    1155
```

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
tgttctgtac atgctcacgt tttac                                          25

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
cacacggtct cacaagacaa cgttggacaa ctgc                                34

<210> SEQ ID NO 11
<211> LENGTH: 37
<212> TYPE: DNA
<213> ORGANISM: Artificial Sequence
<220> FEATURE:
<223> OTHER INFORMATION: primer

<400> SEQUENCE: 11
cacacggtct caatcaaacg aaaagacaac gttggac                             37

<210> SEQ ID NO 12
<211> LENGTH: 66
<212> TYPE: DNA
<213> ORGANISM: Artificial Sequence
<220> FEATURE:
<223> OTHER INFORMATION: primer

<400> SEQUENCE: 12
cttgtcgttt ggtgtctgtt cagggcccag tatcattatg acgttgtacc tgaccttatg    60
actgca                                                               66

<210> SEQ ID NO 13

```
<211> LENGTH: 58
<212> TYPE: DNA
<213> ORGANISM: Artificial Sequence
<220> FEATURE:
<223> OTHER INFORMATION: primer

<400> SEQUENCE: 13
gtcataaggt caggtacaac gtcataatga tactgggccc tgaacagaca ccaaacga        58

<210> SEQ ID NO 14
<211> LENGTH: 57
<212> TYPE: DNA
<213> ORGANISM: Artificial Sequence
<220> FEATURE:
<223> OTHER INFORMATION: primer

<400> SEQUENCE: 14
tgatgtctgt tcagggccca gtatcattat gacgttgtac ctgaccttat gactgca         57

<210> SEQ ID NO 15
<211> LENGTH: 49
<212> TYPE: DNA
<213> ORGANISM: Artificial Sequence
<220> FEATURE:
<223> OTHER INFORMATION: primer

<400> SEQUENCE: 15
gtcataaggt caggtacaac gtcataatga tactgggccc tgaacagac                  49
```

MODIFIED STEROL ACYLTRANSFERASES

CROSS-REFERENCE TO RELATED APPLICATIONS

This application is the U.S. national phase of International Application No. PCT/EP2019/063076 filed May 21, 2019 which designated the U.S. and claims priority to CH 00627/18 filed May 22, 2018, the entire contents of each of which are hereby incorporated by reference.

REFERENCE TO SEQUENCE LISTING SUBMITTED ELECTRONICALLY

The content of the electronically submitted sequence listing (Name: 4662-4076_Sequence_Listing.txt; Size: 26 kilobytes) filed with the application is incorporated herein by reference in its entirety.

The present invention is related to modified sterol acyltransferase enzymes with improved activity and/or specificity towards acylation of the vitamin D3 precursor 7-dehydrocholesterol (7-DHC) to be used in biotechnological production of vitamin D3. The invention further relates to a yeast strain expressing said modified enzymes and their use in a process for production of vitamin D3 or derivatives and/or metabolites thereof.

Vitamin D3 (also known as cholecalciferol or calciol) can be synthesized in the skin of mammals from provitamin D3 (also known as 7-dehydrocholesterol or 7-DHC) which is product of cholesterol biosynthesis upon exposure to UV light, whereby 7-DHC is photochemically converted into provitamin D3, which isomerizes at body temperature to the biologically active form vitamin D3. In the liver, vitamin D3 is converted to the biologically inactive 25-hydroxyvitamin D3 (also known as calcidiol, calcifediol, 25-hydroxycholecalciferol, 25-OH-D3 or HyD), which is the major circulating form of vitamin D3. Further hydroxylation occurs in the kidney.

For industrial production of vitamin D3, both chemical and biotechnological synthesis is (in principle) available. Chemical synthesis starts with cholesterol isolated from e.g. wool fat which is dehydrogenated into 7-DHC, an important intermediate in both chemical and biotechnological synthesis. Through exposure by UV-light and further purification/extraction steps 7-DHC is converted into vitamin D3. Modified yeast stains can be used for biosynthesis of 7-DHC, wherein acetyl-CoA is converted in a multi-step enzymatic process into 7-DHC. Said enzymatic conversion takes place in the endoplasmatic reticulum of the yeast. Excessive amounts of sterols, including 7-DHC and precursors thereof, not required in cellular membranes, are toxic to the yeast and are thus stored as steryl esters into intracellular organelles (so-called lipid bodies) from which they can be further isolated. The equilibrium between free sterols and those stored in the lipid bodies (mainly in the form of steryl esters) is triggered via the action of several proteins (enzymes), including action of sterol acyltransferases. In yeast, particularly Saccharomyces cerevisiae, ester formation of sterols is mainly carried out by the two sterol acyltransferases Are1p and Are2p.

Due to the unspecific action of said sterol acyltransferase enzymes, the steryl ester pool which is stored within the lipid bodies is relatively diverse, including but not limited to e.g. esters of ergosterol, zymosterol, lanosterol, lathosterol, cholesta-5,7,24(25)-trienol, or 7-DHC. Since only cholesta-5,7,24(25)-trienol, a precursor for 7-DHC, and not zymosterol can be used for vitamin D3 synthesis, there is a need for either selective storage of specific esters, such as e.g. esters of 7-DHC, into the lipid bodies and/or for increasing the turnover of intermediates of 7-DHC produced by such a yeast strains which are further converted to vitamin D3 and/or derivatives or metabolites thereof. A particular metabolite which is also in focus of the present invention is 25-hydroxyvitamin D3.

Thus, it is an ongoing task to generate host cells, such as yeast capable of producing sterols, with high productivity/specificity for 7-DHC and/or reduced accumulation of side-products/intermediates including zymosterol, lanosterol or lathosterol, in particular esters of such intermediates stored in the lipid bodies.

Surprisingly, we now found that the specificity of the sterol acyltransferase activity in the host cell can be shifted towards 7-DHC via introduction of certain amino acid substitutions in the sequence of ARE2 and/or ARE1 which will lead to higher productivity and/or product ratio of the host cell towards 7-DHC as important intermediate in vitamin D3 production.

Thus, the present invention is directed to modified enzymes with sterol acyltransferase activity, i.e. modified sterol acyltransferases, particularly activity of sterol acyltransferase isoform Are1p and/or Are2p, comprising one of more amino acid substitution(s) at (a) position(s) corresponding to residues selected from 592 and/or 595 in the polypeptide according to SEQ ID NO:1, said modified enzyme has increased specificity towards 7-DHC over side-products/intermediates including zymosterol.

The polypeptide according to SEQ ID NO:1, showing ARE1 activity, including polynucleotides encoding such polypeptide according to SEQ ID NO:1, has been isolated from *Saccharomyces cerevisiae*. The polypeptide according to SEQ ID NO:3, showing ARE2 activity, including polynucleotides encoding such polynucleotide according to SEQ ID NO:3, has been isolated from *Saccharomyces cerevisiae*.

The terms "sterol acyltransferase", "acyltransferase", "ARE", "enzyme having acyltransferase activity" or just "enzyme" are used interchangeably herein and refer to enzymes [EC 2.3.1.26], i.e. acyltransferases transferring fatty acyl groups from one molecule to another. Such transfer or enzymatic activity can be measured by means known to the skilled person. Sterol acyltransferases have been isolated from different origins, including mammals, yeast or plants. Both ARE1 and ARE2 are capable of acylating sterols such as e.g. zymosterol and/or 7-DHC to the respective esters. As used herein, a "modified" enzyme, i.e. modified acyltransferase, has a preferred activity and/or specificity towards esterification of 7-DHC compared to esterification of e.g. zymosterol and/or improved formation of total sterol esters, including e.g. 7-DHC or zymosterol. Preferred acyltransferase isoforms are Are1p or Are2p. A "non-modified" sterol acyltransferase, particularly ARE1 and ARE2, as used herein refers to the respective endogenous enzymes not carrying one or more amino acid substitution(s) as defined herein.

As used herein, a host cell carrying a modified sterol acyltransferase activity as defined herein, particularly ARE2 and/or ARE1 comprising one or more amino acid substitution(s) as defined herein, is referred to as "modified" host cell. The respective host cell carrying a non-modified sterol acyltransferase activity, i.e. encoding the wild-type ARE1 and/or ARE2 genes, is referred to as "non-modified" host cell.

As used herein, the terms "zymosterol", "lanosterol", "lathosterol", "cholesta-5,8,24(25)-trienol", "cholesta-5,7,24(25)-trienol", or "7-DHC" specifying vitamin D3 intermediates include both the free form and the ester form of said compounds. As used herein, a sterol mix contains 7-DHC and "side-products" or intermediates, including but not limited to zymosterol, lanosterol, lathosterol, cholesta-5,8,24(25)-trienol, or cholesta-5,7,24(25)-trienol.

As used herein, a "cholesterol-producing yeast" cannot produce ergosterol anymore but cholesterol products, including, but not limited to cholesta-5,7,24(25)-trienol, cholesta-5,8,24(25)-trienol, cholesta-7,24(25)-dienol, 7-DHC or zymosterol. Particularly, this might be achieved via introduction of erg5erg6 double-knock out.

In one embodiment, the modified enzyme as defined herein, in particular modified ARE1 activity, comprises an amino acid substitution at a position corresponding to residue 592 in the polypeptide according to SEQ ID NO:1, preferably substitution of phenylalanine by leucine (F592L). Preferably, the enzyme having modified ARE1 activity is originated from *Saccharomyces*, such as *S. cerevisiae*. Using said modified ARE1 enzyme, the ratio 7-DHC to zymosterol in the sterol mix could be increased by at least about 15% compared to a strain expressing the non-modified endogenous ARE1.

In one embodiment, the modified enzyme as defined herein, in particular modified ARE1 activity, comprises an amino acid substitution at a position corresponding to residue 595 in the polypeptide according to SEQ ID NO:1, preferably substitution of phenylalanine by leucine (G595D). Preferably, the enzyme having modified ARE1 activity is originated from *Saccharomyces*, such as *S. cerevisiae*. Using said modified ARE1 enzyme, the ratio 7-DHC to zymosterol in the sterol mix could be more than doubled, i.e. increased by at least about 55% compared to a strain expressing the non-modified endogenous ARE1.

In a further embodiment, the modified enzyme as defined herein, in particular modified ARE2 activity, comprises an amino acid substitution at a position is corresponding to residue 624 in the polypeptide according to SEQ ID NO:3, preferably substitution of phenylalanine by leucine (F624L). Preferably, the enzyme having modified ARE2 activity is originated from *Saccharomyces*, such as *S. cerevisiae*. Using said modified ARE2 enzyme, the ratio 7-DHC to zymosterol in the sterol mix could be increased by at least about 15% compared to a strain expressing the non-modified endogenous ARE2.

In a further embodiment, the modified enzyme as defined herein, in particular modified ARE2 activity, comprises an amino acid substitution at a position corresponding to residue 627 in the polypeptide according to SEQ ID NO:3, preferably substitution of glycine by aspartic acid (G627D). Preferably, the enzyme having modified ARE2 activity is originated from *Saccharomyces*, such as *S. cerevisiae*. Using said modified ARE2 enzyme, the ratio 7-DHC to zymosterol in the sterol mix could be increased by at least about 15% compared to a strain expressing the non-modified endogenous ARE2.

The described amino acid substitution(s) at a position corresponding to residue F592L and/or G595D in SEQ ID NO:1 might be combined with further substitutions as defined herein, i.e. substitutions on one or more position(s) corresponding to amino acid residue(s) 624 and/or 627 in the polypeptide according to SEQ ID NO:3 and as described herein. Preferably, the amino acid substitution at a position corresponding to residue F592L in SEQ ID NO:1 might be combined with further substitutions, such as amino acid substitutions at position(s) corresponding to G595D in SEQ ID NO:1 and/or F624L in SEQ ID NO:3 and/or G627D in SEQ ID NO:3. A preferred modified enzyme is an enzyme having ARE1 activity and comprises at least an amino acid substitution at a position corresponding to G595D in SEQ ID NO:1, showing at least about 30, 35, 40, 45% higher 7-DHC titers, at least about 15, 20, 25, 30% less zymosterol in the sterol mix with a percentage of 7-DHC in the sterol mix of about 70-76%.

As used herein, the activity of ARE1 and/or ARE2 is modified. This might be achieved by, e.g. introducing (a) mutation(s) into the endogenous gene coding for ARE1 and/or ARE2, i.e. amino acid substitution(s) on one or more positions as described herein. The skilled person knows how to genetically manipulate a yeast cell resulting in modification of ARE1 and/or ARE2 activity. These genetic manipulations include, but are not limited to, e.g. gene replacement, gene amplification, gene disruption, transfection, transformation using plasmids, viruses, or other vectors.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

The present invention is particularly directed to the use of such modified ARE1 and/or ARE2 enzymes as defined herein in a process for production of 7-DHC, an intermediate for vitamin D3. Preferably, the modified enzymes of the present invention are introduced and/or expressed in a suitable host cell, such as yeast, preferably sterol-producing yeast, in particular cholesterol-producing yeast cell, such as selected from *Saccharomyces cerevisiae, Schizosaccharomyces* spp., *Pichia* spp., *Klyuveromyces* spp., *Hansenula* spp. or *Yarrowia lipolytica*, preferably *S. cerevisiae*. The modified host is used for production of 7-DHC, which might be further converted into vitamin D3 and/or 25-hydroxyvitamin D3.

A suitable host cell might be further modified to further increase production of 7-DHC, an important intermediate towards biosynthesis of vitamin D3, and/or reduce accumulation of side-products.

Thus, in one embodiment the invention is directed to a yeast strain having modified ARE1 and/or ARE2 activity and furthermore wherein ERG5 and ERG6 are inactivated. The yeast cell might be further modified via expression of a heterologous enzyme having C24-reductase activity, particularly selected from EC 1.3.1.72, such as a heterologous C24-reductase that is active on cholesta-7,24-dienol, zymosterol, or trienol (e.g. cholesta-5,7,25-trienol), preferably a plant or vertebrate sterol Δ24-reductase, more preferably from vertebrate source, even more preferably from human, pig, dog, mouse, rat, horse, *Danio rerio* or any known source, as long as it can be expressed within said yeast cell. Most preferably, the sterol Δ24-reductase is selected from *Danio rerio*, rat or human. The sequences expressing said sterol Δ24-reductase enzymes are publicly available, including but not limited to UniProtKB/Swiss-Prot reference Q15392, Q60HC5, Q8VCH6, Q5BQE6, Q39085 or P93472 (see e.g. WO2003064650). Using such a yeast strain, the percentage of 7-DHC present in the sterol mix is in the range of about 70 or more, preferably such as 75, 80, 88, 90, 95, 98% based on the total amount of sterols.

In another embodiment, the host cell according to the present invention might be further modified via introduction of homologs of endogenous enzymes involved in biosynthesis of 7-DHC, such as e.g. C5-sterol desaturase (ERG3) and/or C8-sterol isomerase (ERG2), resulting in increased specificity and/or productivity of 7-DHC with reduced accumulation of side-products or vitamin D3 intermediates, including but not limited to zymosterol, lanosterol and/or lathosterol. Preferably, the modified host cell as defined herein comprises a heterologous ERG2 and/or ERG3, wherein the ERG2 is preferably selected from *Ustilago maydis* (sequence derived from UniProtKB P32360), and/or wherein the ERG3 is preferably selected from *Pichia pastoris* (sequence derived from UniProtKB C4QY87) or *Schizosaccharomyces pombe* (sequence derived from UniProtKB 094457). Strains comprising both ERG2 and ERG3 homologs together with the modified ARE1 and/or ARE2 as defined herein produce a sterol mix with over about 80% 7-DHC percentage and increased 7-DHC to cholesta-8-enol and/or lathosterol ratio by at least about 15 to 20%. Even more preferred is a modified strain as defined herein further comprising two or more copies of either ERG2 and/or ERG3 homologs as described above.

In a particular embodiment, the invention relates to a process for improving a host cell towards production of 7-DHC, wherein a modified host cell as defined herein, i.e. modified via introduction of one or more amino acid substitutions in sterol acyltransferases ARE1 and/or ARE2 as defined herein, in particular a cholesterol-producing yeast cell, preferably a yeast cell in which ERG5 and ERG6 are inactivated and wherein optionally a heterologous enzyme having C-24-reductase activity as defined herein is expressed, and/or wherein optionally homologs of endogenous ERG2 and/or ERG3 are expressed, wherein the host cell is improved such that the percentage of 7-DHC in the total amount of sterol produced by said host cell is increased from to about at least 70, 75, 80%, preferably 88, 90, 95, 98%, in particular wherein the ratio of 7-DHC to side-products including zymosterol and cholesta-8-enol is increased by at least about 5, 10, 15, 18, 20, 25% and as compared to a yeast strain expressing the non-modified, i.e. wild-type ARE1 and/or ARE2 activity.

In one aspect of the present invention, a host cell comprising modified ARE1 and/or ARE2 activity as defined herein is used in a process for production of vitamin D3 precursor 7-DHC. The modified host cell may be cultured in an aqueous medium supplemented with appropriate nutrients under aerobic or anaerobic conditions and as known by the skilled person for the respective cholesterol-producing host cells. Optionally, such cultivation is in the presence of proteins and/or co-factors involved in transfer of electrons, as known in the art. The cultivation/growth of the host cell may be conducted in batch, fed-batch, semi-continuous or continuous mode. Depending on the host cell, preferably, production of vitamin D3 and precursors thereof such as 7-DHC can vary, as it is known to the skilled person. Cultivation and isolation of 7-DHC and other intermediates in production of vitamin D3 is described in e.g. WO2011067144 or WO2017108799. The 7-DHC might be isolated and/or optionally further purified from the sterol mix and might be further converted to vitamin D3 and/or 25-hydroxyvitamin D3 using methods known in the art.

Using a host cell as described herein, the substrate-specificity of sterol acyltransferase activity could be shifted towards 7-DHC, leading to a percentage of at least about 70% 7-DHC in the total sterols produced by said host cell, with titers of up to about 10 g/l or more 7-DHC produced after about 100 h fermentation under suitable culture conditions.

The terms "ARE1" and "Are1p", "ARE2" and "Are2p", "ERG5" and "Erg5p", "ERG6" and "Erg6p" are used interchangeably herein and refer to a polypeptide encoded by the respective genes are1, are2, erg5, and erg6. For the purpose of the present invention, the cholesterol-producing yeast cell is modified such that it does show modified activity of ARE1 and/or ARE2, e.g. carries a modification in either endogenous ARE1, ARE2 or both, leading to modified specificity of ARE1 and/or ARE2, wherein said modification is achieved via introduction of one or more amino acid substitutions as defined herein.

Genes encoding ERG5, ERG6, ARE1, ARE2, ERG2, ERG3, or sterol Δ24-reductase (ERG4), cultivation and genetic engineering of the yeast cell as used herein are known and described in e.g. U.S. Pat. No. 7,608,421.

As used herein, the terms "C-24-reductase" or "Δ24-reductase" are used interchangeably herein. In yeast, this enzyme is encoded by erg4 and is active on the methyl-group of the carbon atom on position 24. Trienol, which does not exhibit such methyl-group on said position, is therefore not an acceptable substrate for the yeast ERG4.

The terms "C-8 sterol isomerase", "delta 8,7-isomerase", or "enzyme having C-8 sterol isomerase" are used interchangeably herein and refer to enzymes which are capable of catalyzing the conversion of cholesta-8-enol into cholesta-7-enol and/or zymosterol into cholesta-7,24-dienol. In yeast, this enzyme is encoded by erg2. A preferred ERG2 homolog to be used in a modified host cell according to the present invention is a polypeptide having at least about 41%, such as e.g. at least 44, 45, 48, 49, 53, 56, 60, 70, 80, 90, 92, 95, 98 or up to 100% identity to SEQ ID NO:5 showing C-8 sterol isomerase activity and including polynucleotides encoding such polypeptide, obtainable from *Ustilago maydis*. Particularly, 1 or more copies, such as at least about 1, 2, 3, 5, of said ERG2 homolog are expressed in a modified host cell as defined herein.

The terms "C-5 sterol desaturase", "enzyme having C-5 sterol desaturase are used interchangeably herein and refer to enzymes which are capable of catalyzing the conversion of cholesta-8-enol into cholesta-7,24-dienol and/or cholesta-7-enol into cholesta-5,7,24-trienol and/or 7-DHC. In yeast, this enzyme is encoded by erg3. A preferred ERG3 homolog to be used in a modified host cell according to the present invention is a polypeptide having at least about 45%, such as e.g. at least 50, 52, 60, 70, 80, 90, 92, 95, 98 or up to 100% identity to SEQ ID NO:7 showing C-5 sterol desaturase activity and including polynucleotides encoding such polypeptide, obtainable from *Pichia pastoris* or *Schizosaccharomyces pombe*. Particularly, 1 or more copies, such as at least 1, 2, 3, 5, of said ERG3 homolog are expressed in a modified host cell as defined herein.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person is aware of the fact that plant-derived enzymes might contain a chloroplast targeting signal which is to be cleaved via specific enzymes, such as e.g. chloroplast processing enzymes (CPEs).

The ARE2 and ARE1 enzymes/homologs, as defined herein also encompass enzymes carrying amino acid substitution(s) which do not alter enzyme activity, i.e. which show the same properties with respect to the wild-type enzyme and catalyze acylation of sterols as defined herein. Such mutations are also called "silent mutations", which do not alter the (enzymatic) activity of the enzymes as described herein.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, such as e.g. by HPLC.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

In particular, the present invention features the present embodiments:

(1) A modified enzyme having sterol acyltransferase activity comprising one of more amino acid substitution(s) at (a) position(s) corresponding to residues selected from 592 and/or 595 in the polypeptide according to SEQ ID NO:1, preferably substitution corresponding to F592L and/or G595D.

(2) A modified enzyme as defined herein and as of embodiment (1) catalyzing the esterification of sterols comprising 7-dehydrocholesterol (7-DHC) and zymosterol, wherein the ratio of 7-DHC to zymosterol in the sterol esters is increased by at least about 15% compared to the ratio of 7-DHC to zymosterol in the catalysis using the respective non-modified enzyme.

(3) A modified enzyme as defined herein and as of embodiment (1) or (2), wherein the amino acid substitution is selected from G595D.

(4) A host cell, preferably a yeast, more preferably a sterol-producing yeast, even more preferably a cholesterol-producing yeast, comprising a modified enzyme as defined herein and as of embodiments (1), (2), (3).

(5) A host cell as defined herein and as of embodiment (4) used for production of a sterol mix comprising 7-DHC and zymosterol, wherein the ratio of 7-DHC to zymosterol is increased by at least about 15% compared to a host cell wherein expressing a non-modified enzyme.

(6) A host cell as defined herein and as of embodiment (4) or (5), wherein ERG5 and ERG6 are inactivated.

(7) A host cell according as defined herein and as of embodiment (4), (5), (6), wherein the cell expresses a heterologous enzyme selected from EC 1.3.1.72 having sterol Δ24-reductase activity, preferably wherein the heterologous enzyme is originated from plant or vertebrate, more preferably originated from human, pig, dog, mouse, rat, horse or *Danio rerio*.

(8) A host cell as defined herein and as of embodiments (4), (5), (6), (7), wherein the host cell is selected from the group consisting of *Saccharomyces, Schizosaccharomyces, Pichia, Kluyveromyces, Hansenula*, and *Yarrowia*, preferably selected from *Saccharomyces cerevisiae, Schizosaccharomyces* spp., *Pichia* spp., *Kluyveromyces* spp., *Hansenula* spp. or *Yarrowia lipolytica*.

(9) A process for reducing the percentage of zymosterol in a sterol mix comprising zymosterol and 7-DHC comprising cultivating a host cell as defined herein and as of embodiments (4), (5), (6), (7), (8) under suitable conditions and optionally isolating and/or purifying the 7-DHC from the sterol mix.

(10) A process for increasing the percentage of 7-DHC in a sterol mix comprising 7-DHC and zymosterol comprising cultivating a host cell as defined herein and as of embodiments (4), (5), (6), (7), (8) under suitable conditions and optionally isolating and/or purifying the 7-DHC from the sterol mix.

(11) A process for production of 7-DHC comprising enzymatic conversion of acetyl-CoA into a sterol mix comprising zymosterol and 7-DHC with a host cell as defined herein and as of embodiments (4), (5), (6), (7), (8), (9), (10), wherein the percentage of 7-DHC in the sterol mix is at least about 70%.

(12) A process as defined herein and as of embodiment (11), wherein the 7-DHC is further converted into vitamin D3.

(13) A process as defined herein and as of embodiment (11) or (12), wherein the 7-DHC is further converted into 25-hydroxyvitamin D3.

(14) Use of a modified enzyme as defined herein and as of embodiments (1), (2), (3) or a host cell as defined herein and as of embodiments (4), (5), (6), (7), (8), (9), (10), in a process for production of 7-DHC, wherein the 7-DHC is isolated from a sterol mix comprising zymosterol and 7-DHC, and wherein the ratio of 7-DHC to zymosterol is increased by at least about 15% compared to a process using the respective non-modified enzyme and host cell, respectively.

The following examples are illustrative only and are not intended to limit the scope of the invention in any way.

EXAMPLES

Example 1: General Methods, Strains and Plasmids

All basic molecular biology and DNA manipulation procedures described herein were generally performed according to Sambrook et al. (1989. Molecular Cloning: A Laboratory Manual. Cold Spring Harbor Laboratory Press: New York) or Ausubel et al. (1998. Current Protocols in Molecular Biology. Wiley: New York). Genotyps of the used *S. cerevisiae* strains and plasmids are listed in Table 1 and 2. *Saccharomyces cerevisiae* 7-DHC producing strain Y2140 was constructed starting from a wildtype CEN.PK background strain. Into this wildtype strain an erg5 disruption cassette was transformed that contained a codon-optimized gene for a sterol 24-reductase from zebrafish flanked by a PGK1 promoter and a CYC1 terminator in combination with TRP1. Subsequently, an erg6 disruption cassette was transformed that contained the gene for a sterol 24-reductase from rat flanked by a TDH3 promoter and a PGK1 terminator in combination with LEU2. All mentioned strains are MATα, and harbor an overexpressed copy of the truncated constitutively active HMG-CoA reductase gene (tHMG1).

TABLE 1

*Saccharomyces cerevisiae* strains.

| Y2159 | erg5Δ::PGK1p-S24R2-CYC1t-TRP1<br>erg6Δ::TDH3p-S24R1-PGK1t-URA3<br>erg4Δ::Hyg$^R$ TDH3p-tHMG1 | Classical and standard molecular and genetic techniques |
|---|---|---|
| Y2017 | erg5Δ::PGK1p-S24R2-CYC1t-TRP1<br>erg6Δ::TDH3p-S24R1-PGK1t-URA3<br>erg4Δ::PGK1p-Scer-ARE1-CYC1t-LEU2<br>TDH3p-tHMG1 | Targeted replacement with LEU2 cassette |
| Y2157 | erg5Δ::PGK1p-S24R2-CYC1t-TRP1<br>erg6Δ::TDH3p-S24R1-PGK1t-URA3<br>erg4Δ::PGK1p-Scer-are1 F592L-CYC1t-LEU2<br>TDH3p-tHMG1 | Targeted replacement with LEU2 cassette |
| Y2159 | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 | Targeted replacement with LEU2 cassette |

TABLE 2 plasmids used for construction of ARE mutations. "Scer" means *Saccharomyces cerevisiae*.

| Plasmid | Backbone | Insert | Oligos or source | SEQ ID NO |
|---|---|---|---|---|
| pHyD459 | pHyD445 | Scer-ARE1 | LEU2 insertion | |
| pMB7584 | pHyD459 | Scer-are1 F592L | MO10013 & MO10014,<br>MO10016 & MO10017 | 16 & 17<br>19 & 20 |

TABLE 2-continued plasmids used for construction of ARE mutations. "Scer" means *Saccharomyces cerevisiae*.

| Plasmid | Backbone | Insert | Oligos or source | SEQ ID NO |
|---|---|---|---|---|
| pMB7585 | pHyD459 | Scer-are1 G595D | MO10013 & MO10015 | 16 & 18 |

Example 2: Construction of ARE1-WT Plasmid pHyD459

WT *S. cerevisiae* ARE1 was synthesized by DNA2.0, incorporating an XbaI site at the 5' end (TCTAGAACAAAatg . . . ) and a PstI site at the 3' end. This was cloned into an erg4Δ::Hyg$^R$ deletion plasmid using unique XbaI and PstI sites. LEU2 was subsequently used to replace the HygR moiety via a Kpnl-Agel cloning.

Example 3: Cloning of ARE1 Mutant Genes

*S. cerevisiae* ARE1 mutant variant pMB7584 (F592L) was generated by ligating a BsrGI-BsaI-cleaved PCR product generated from ARE1 (oligos according to SEQ ID NO:16 & 17) with a double-stranded oligo derived by annealing SEQ ID NO:19 and 20 into BsrGI-PstI-cleaved pHyD459. Similarly, *S. cerevisiae* ARE1 mutant variant pMB7585 (G595D) was generated by ligating a BsrGI-BsaI-cleaved PCR product generated from ARE1 (oligos according to SEQ ID NO:16 a 18) with a double-stranded oligo derived by annealing SEQ ID NO:21 and 22 into BsrGI-PstI-cleaved pHyD459. The oligos as well as further sequences used herein are listed in the sequence listing.

Example 3: Introduction of ARE1 WT and Mutant Genes into *Saccharomyces cerevisiae*

To the test the impact of the mutant ARE1 genes in 7-DHC production in comparison to the WT gene, strain Y2140 was transformed with three different constructs:

(1) a SalI fragment of plasmid pHyD459 which is an erg4 disruption construct harboring the WT ARE1 gene under the control of the PGK1 promoter and LEU2.on construct harboring the WT ARE1 gene under the control of the PGK1 promoter and LEU2;

(2) a SalI fragment of plasmid pMB7584 which is an erg4 disruption construct harboring the are1 F592L gene under the control of the PGK1 promoter and LEU2are1 F592L gene under the control of the PGK1 promoter and LEU2;

(3) a SalI fragment of plasmid pMB7585 which is an erg4 disruption construct harboring the are1 G595D gene under the control of the PGK1 promoter and LEU2are1 G595D gene under the control of the PGK1 promoter and LEU2.

Transformants were selected on (minimal media) at 30° C. and screened for hygromycin sensitivity. Strains resulting from these transformations are listed in Table 1 above. These strains were subsequently assayed for their 7-DHC productivity and overall 7-DHC sterol purity as described in Example 4 below.

Example 4: HPLC Analysis of Sterols in ARE Mutant Strains

Strains to be tested were initially plated onto YPD agar and incubated for 48 hours at 30° C. Two milliliters YPD pre-cultures were inoculated from these plates and grown on a roller wheel for 24 hours at 30° C. In a 24-well microtiter plate, 0.8 mL of YPD+10 g/L ethanol were inoculated from the preculture to a final $OD_{600}$ of 0.5. Microtiter plates were grown at 30° C. in a humidified environment and shaking at 800 rpm on a shaker with an orbit of 3 mm. At 24 and 48 hours post-inoculation, 16 µl ethanol was added to each well as a feed. At 72 hours post-inoculation the cells were sampled for sterol content.

For extraction of sterols from the cultures eighty microliters of whole broth was pipetted into a 2-mL Precellys tube with glass beads. Eight hundred microliters of saponification solution (5% KOH in ethanol) was added, and samples were placed into a Precellys 24 Homogenizer and agitated at 6500 rpm for 3 cycles at 15 seconds per cycle. Sixty microliters of glacial acetic acid were then added and the tubes were centrifuged for 1 minute at top speed. The supernatant was assayed via HPLC for sterol content (see Table 3).

TABLE 3 ratios of 7-DHC to selected sterol intermediates in control and ARE1 and/or ARE2 mutant strains. "Lano-/latho" means a mix of lanosterol and lathostherol, "zym" means zymosterol. Numbers are in mg/ml of sterols.

| Mutant | 7-DHC | lano-/latho | Cholesta-8-enol | zym | Ratio 7-DHC to zym | Ratio 7-DHC to lano/latho |
|---|---|---|---|---|---|---|
| ARE1 wt | 1060 | 70 | 99 | 92 | 12 | 15 |
| are2-F624L | 1090 | 35 | 122 | 80 | 14 | 31 |
| are2-G627D | 1141 | 50 | 140 | 82 | 14 | 23 |
| are1-F592L | 1240 | 62 | 143 | 105 | 14 | 20 |
| are1-G595D | 1448 | 104 | 152 | 77 | 19 | 14 |

As the result of a screen of various *S. cerevisiae* Are1 mutants, the inventors found a number of Are1 variants that, when expressed, produce 7-DHC with a higher overall productivity, less accumulation of sterol side products (zymosterol, lathosterol, lanosterol, cholesta-8-enol, etc), or both.

The invention claimed is:

1. A process for production of 7-dehydrocholesterol (7-DHC) comprising enzymatically converting acetyl-CoA into a sterol mix comprising zymosterol and 7-DHC with a host cell, wherein the percentage of 7-DHC in the sterol mix is at least 70%, and wherein the host cell is a recombinant host cell that expresses a modified enzyme selected from EC 2.3.1.26 having sterol acyltransferase activity comprising one or two amino acid substitutions at positions corresponding to residues 592 and 595 in the polypeptide according to SEQ ID NO:1, wherein the substituted amino acid corresponding to residue 592 in the polypeptide according to SEQ ID NO:1 is leucine and the substituted amino acid corresponding to residue 595 in the polypeptide according to SEQ ID NO:1 is aspartic acid.

2. The process of claim 1, wherein the 7-DHC is further converted into vitamin D3.

3. The process of claim 1, wherein the 7-DHC is further converted into 25-hydroxyvitamin D3.

4. The process of claim 1, wherein the modified enzyme comprises a modified yeast ARE1 or ARE2 polypeptide.

5. The process of claim 4, wherein the ratio of 7-DHC to zymosterol in the sterol mix is increased by at least 15% compared to a sterol mix produced by the corresponding process using the corresponding host cell that expresses the corresponding non-modified enzyme selected from EC 2.3.1.26 having sterol acyltransferase activity.

6. The process of claim 4, wherein the modified enzyme comprises a modified yeast ARE1 or ARE2 polypeptide, wherein the yeast is selected from the group consisting of *Saccharomyces cerevisiae*, *Schizosaccharomyces* spp., *Pichia* spp., *Klyuveromyces* spp., *Hansenula* spp. and *Yarrowia lipolytica*.

7. The process of claim 6, wherein the modified enzyme comprises a modified *Saccharomyces cerevisiae* ARE1 or ARE2 polypeptide.

8. The process of claim 7, wherein the modified enzyme comprises the amino acid sequence of SEQ ID NO: 1 comprising the F592L and/or G595D substitution or the amino acid sequence of SEQ ID NO: 3 comprising the F624L and/or G627D substitution.

9. The process of claim 4, wherein the host cell is a recombinant cholesterol-producing yeast cell.

10. The process of claim 4, wherein the host cell is selected from the group consisting of *Saccharomyces cerevisiae*, *Schizosaccharomyces* spp., *Pichia* spp., *Kluyveromyces* spp., *Hansenula* spp. and *Yarrowia lipolytica*.

* * * * *